Jan. 24, 1967 R. BERGERON Plant Pat. 2,703
MOCK ORANGE (PHILADELPHUS) PLANT
Filed Nov. 25, 1964
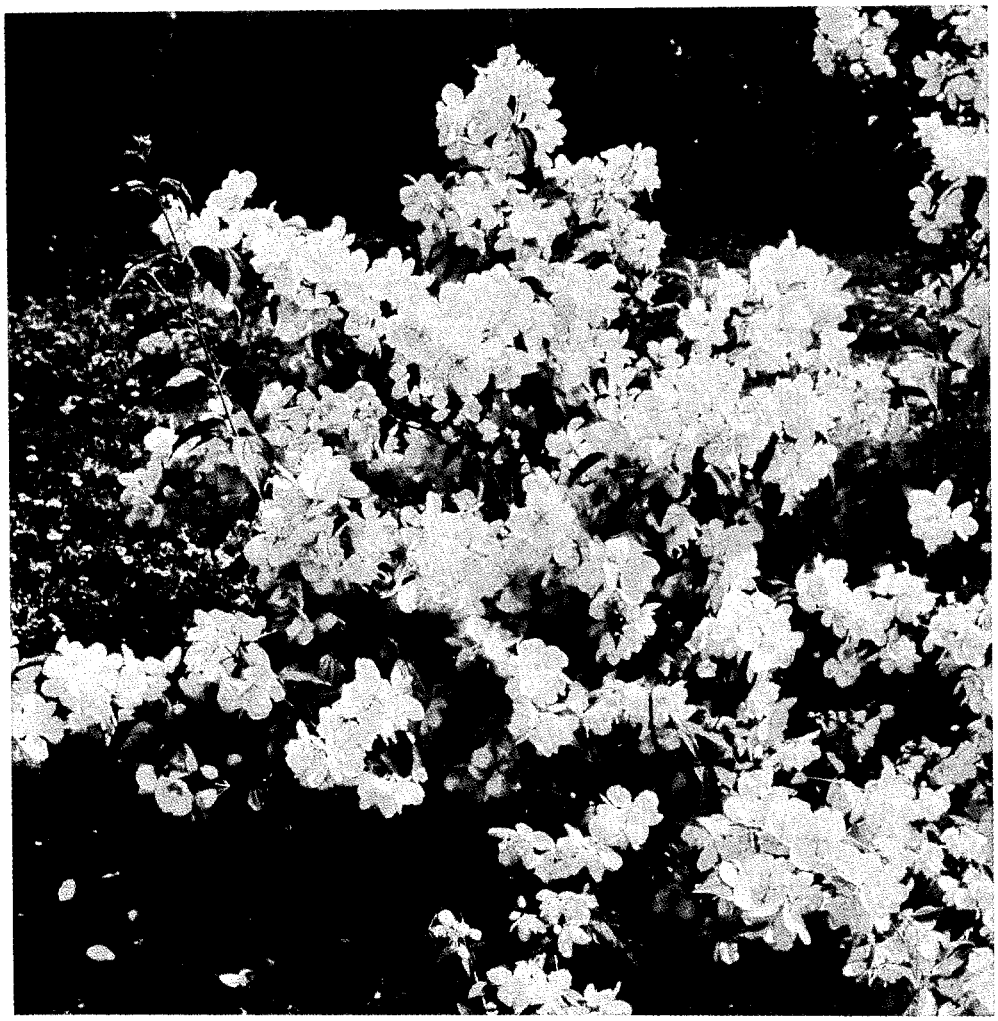
Inventor.
Roland Bergeron
By: Robb & Robb
Attorneys.

United States Patent Office

Plant Pat. 2,703
Patented Jan. 24, 1967

2,703
MOCK ORANGE (PHILADELPHUS) PLANT

Roland Bergeron, Orleans, France, assignor, by mesne assignments, to Gulf Stream Products, Inc., Wachapreague, Va., a corporation of Virginia Filed Nov. 25, 1964, Ser. No. 414,038
1 Claim. (Cl. Plt.—54)

The present invention relates to a new and distinct variety of mock orange (Philadelphus) plant, which was orginated by me by crossing the variety known as Philadelphus "Banniere" (unpatented) with the variety known as Philadelphus "Conquette" (unpatented), the former being the seed parent and the latter being the pollen parent.

As the result of this breeding, I have produced a new variety of mock orange which is differentiated from its parents, as well as from all other varieties of which I am aware, as evidenced from the following unique combination of characteristics which are outstanding therein:

(1) A dwarfish low-growing shrub habit of growth which reaches a height of only 4 or 5 feet;

(2) A free-flowering habit; and (3) Abundant production of large white semi-double flowers borne in clusters all along the branches, the weight of said flowers causing the branches to arch gracefully and resulting in complete coverage of the entire plant by the flowers which gives a very showy and attractive mass effect.

My new variety of mock orange makes a splendid addition to the low-growing flowering shrubs commonly used for garden and landscape plantings. Its flowers are larger than those of many varieties, and the flowers are produced more freely all along the stems so that during the blooming season the plants are entirely covered with flowers, unlike the more sparse flowers of the parent varieties. This coverage is attributed at least in part to the arching of the branches as the result of the heavy weight of the abundant flowers, and makes the entire plant very showy.

Asexual reproduction of my new variety by cuttings, as performed by me in France, and also on my behalf at Wachapreague, Virginia, U.S.A., shows that the foregoing characteristics and distinctions come true to form and are established and transmitted through succeeding propagations.

The accompanying drawings shows a typical specimen plant of the new variety, as depicted in black and white which is sufficient to illustrate the flowers and foliage by reason of the fact that the pure white flower color and the light green color of the foliage are not significantly different from other common mock orange varieties.

The following is a detailed description of my new mock orange variety, with color terminology in accordance with Koster's Color Guide, except where color terms of ordinary dictionary significance are obvious, as based upon observations made from specimens grown in France and at Wachapreague, Virginia, U.S.A.:

*Plant*

Type: Dwarfish shrub, with height ranging from 4 to 5 feet.

Parentage: Seedling.

*Seed parent.*—Philadelphus "Banniere."

*Pollen parent.*—Philadelphus "Conquette."

Propagation: Holds its distinguishing characteristics through succeeding propagations by cuttings.

Growth habit: Dwarfish; relatively low-growing; gracefully arching branches.

Foliage:

*Size.*—Medium; length 1½ inches; width ¾ inch.

*Quantity.*—Normal; clothes the plant well.

*Color.*—Upper surface—near Spinach Green, Plate 75. Under surface—near Apple Green, Plate 77.

*Shape.*—Oval pointed.

*Texture.*—Smooth; thin.

*Flower*

Blooming habit: Very free.

Blooming season: During month of May; from about May 18 to June 1 in Virginia.

Flower:

*Size.*—About 2½ to 3 inches in diameter, with the panicles averaging from 8 to 10 flowers each.

*Borne.*—In clusters.

*Form.*—Substantially flat.

*Color.*—Pure white; semi-double.

*Texture.*—Good; firm.

*Fragrance.*—Slight.

*Keeping qualities.*—Good.

*Stamens.*—Prominent.

*General observations*

Hardiness: Has withstood winter temperatures as low as zero degrees F. without damage.

Disease and insect resistance: Has shown no evidence of disease or insect damage, as determined by comparison with other varieties grown in France and the United States.

I claim:

A new and distinct variety of mock orange (Philadelphus) plant, substantially as herein shown and described, characterized particularly as to novelty by the unique combination of a dwarfish low-growing shrub habit of growth, a free-flowering habit, and abundant production of large, semi-double white flowers borne in clusters all along the branches, the weight of said flowers causing the branches to arch gracefully and resulting in complete coverage of the entire plant by the flowers which gives a very showy and attractive mass effect.

References Cited by the Examiner

"Shrubs and Vines for American Gardens," Wyman, Macmillan Co., N.Y., 1949, pp. 219–230 relied on.

ABRAHAM G. STONE, *Primary Examiner.*

R. E. BAGWILL, *Examiner.*